(12) United States Patent
Lamont et al.

(10) Patent No.: US 7,026,134 B2
(45) Date of Patent: Apr. 11, 2006

(54) HAPTENS, IMMUNOGENS AND ANTIBODIES TO OXYCODONE AND ITS METABOLITES

(75) Inventors: John Victor Lamont, Co. Antrim (GB); Robert Ivan McConnell, Co. Antrim (GB); Stephen Peter Fitzgerald, Co. Antrim (GB); El Ouard Benchikh, Co. Antrim (GB); Andrew Philip Lowry, Co. Antrim (GB)

(73) Assignee: Randox Laboratories Ltd., Co. Antrim (GB)

( * ) Notice: Subject to any disclaimer, the term of this patent is extended or adjusted under 35 U.S.C. 154(b) by 434 days.

(21) Appl. No.: 10/323,850

(22) Filed: Dec. 20, 2002

(65) Prior Publication Data

US 2003/0157565 A1 Aug. 21, 2003

(30) Foreign Application Priority Data

Dec. 20, 2001 (GB) .................................... 0130535

(51) Int. Cl.
- *G01N 33/535* (2006.01)
- *C07K 16/44* (2006.01)
- *C12P 21/08* (2006.01)
- *C07D 471/08* (2006.01)

(52) U.S. Cl. ............... 435/7.93; 530/388.9; 530/389.8; 530/404; 530/405; 546/43

(58) Field of Classification Search ................ 530/404, 530/405, 388.9, 389.8; 546/43; 435/7.93
See application file for complete search history.

(56) References Cited

U.S. PATENT DOCUMENTS 4,939,264 A 7/1990 Heiman et al.

FOREIGN PATENT DOCUMENTS

WO  WO 93/20079  10/1993

OTHER PUBLICATIONS

M. Smith et al, J. Analytical Toxicology (2000), 24(7), 522-529.*
R. Fogerson et al, J. Analytical Toxicology (1997), 21(6), 451-458.*
K. Aoki et al, Forensic Science International (1996), 81(2,3), 125-132.*
Findlay, John W.A. et al.; "Relationships between Immunogen Structure and Antisera Specificity in the Narcotic Alkaloid Series" *Clinical Chemistry* vol. 27, No. 9 1981; pp. 1524-1535.
Klein, Peter et al.; "$O^3$-(2-Carbomethoxyallyl) Ethers of Opioid Ligands Derived from Oxymorphone, Naltrexone, Etorphine, Diphrenorphine, Norbinaltorphimine, and Naltrindole. Unexpected $O^3$Dealkylation in the Opioid Radioligand Displacement Assay" *Journal of Medicinal Chemistry* vol. 35, No. 24 1992; pp. 4589-4594.
Lester, M. G. et al.; "Vilsmeier Reactions with Cyclic Ketals of 14-Hydroxydihydrocodeinone and some New Cyclic Derivatives of 14-Hydroxydihydrocodeinone" *Elsevier Science Publishers, Amsterdam* vol. 21, No. 4 1965; pp. 771-778.

* cited by examiner

*Primary Examiner*—Mary E. Ceperley
(74) *Attorney, Agent, or Firm*—Oliff & Berridge, PLC

(57) ABSTRACT

Novel haptens, which can be conjugated to form immunogens, are of formula I, II or III

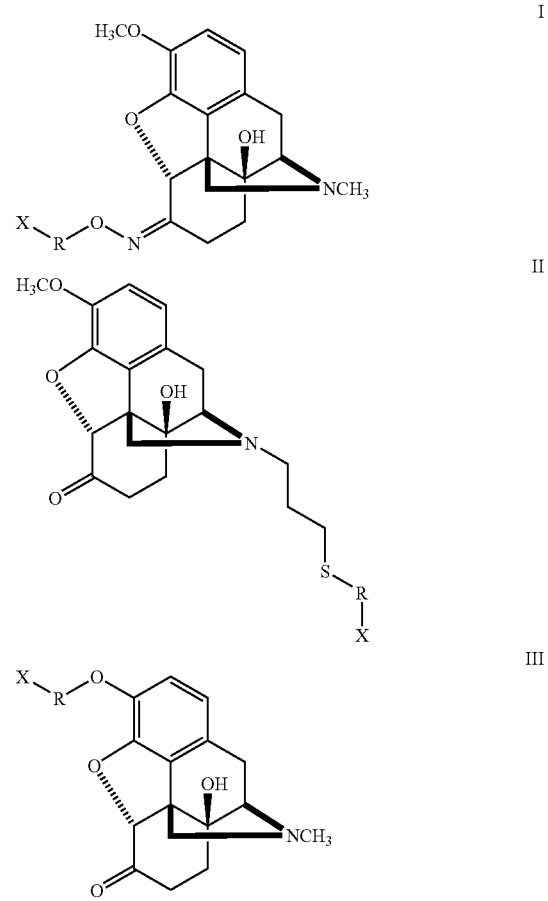

wherein R is a divalent alkyl, cycloalkyl or aryl group having 1 to 10 carbon atoms, and X is a functional group.

16 Claims, No Drawings

HAPTENS, IMMUNOGENS AND ANTIBODIES TO OXYCODONE AND ITS METABOLITES

FIELD OF THE INVENTION

The present invention relates to novel hapten derivatives of oxycodone, and their use in the preparation of immunogens.

BACKGROUND OF THE INVENTION

Specific binding reactions, such as antibody-antigen reactions, have been used extensively in immunoassays to detect and/or quantify a variety of drugs or other compounds of interest in biological fluids. Such immunoassays have been developed for the determination of antigens such as proteins, as well as small molecules (haptens).

Haptens are by definition molecules too small to stimulate the production of antibodies when administered to an animal; that is, haptens by themselves are not immunogenic. However, it is well known that a hapten can be made immunogenic by conjugating it to an appropriate carrier material, which will elicit an immunogenic response when injected into a host animal.

Opiates are a class of alkaloid produced by plants of the poppy family. The most common opiates produced by the poppy plants are morphine and codeine. These opiates have been used for centuries to prevent pain but their continued use leads to addiction. Synthetic analogues of morphine also exhibit the narcotic and addictive properties of the natural opiates and include heroin, hydromorphone, hydrocodone, oxycodone and oxymorphone. These opiates (natural or synthetic) have closely related chemical structures. The illict use of opiates has resulted in a medical requirement for specific antibodies to each opiate, for use in diagnostics to rapidly detect the corresponding opiate and its metabolites in order to monitor and treat opiate addiction.

Oxycodone is a narcotic and analgesic pain-killer, and as a semi-synthetic derivative of morphine can be very addictive. The oxycodone metabolites are noroxycodone and oxymorphone.

To date, the determination of oxycodone and its metabolites in biological fluids has been based mainly on gas chromatography-mass spectrometry (GC-MS) and high-performance liquid chromatography (HPLC). These chromatographic methods provide excellent sensitivity and selectivity but require derivatisation of oxycodone and its metabolites. These methods are, in addition, too costly and time-consuming for use as screening tools.

Radioimmmunoassays are very sensitive, but require radionuclide tracers, for example $^{125}I$ and $^{3}H$, and, in some cases, a preliminary extraction step. There are no known RIAs for oxycodone.

Enzyme-linked immunosorbent assays (ELISAs) are a non-radioactive alternative that could be used for the qualitative and quantitative determination of oxycodone and its metabolites. Again, there are no known ELISAs for oxycodone.

There is a need for oxycodone conjugates and their application to immunoassays for quantifying oxycodone and its metabolites without cross-reactivity to the opiates family in biological fluids.

SUMMARY OF THE INVENTION

According to a first aspect of the present invention, novel oxycodone derivatives, which involve modification of oxycodone at the 3, 6 and N positions, are haptens of formulae I, II and III

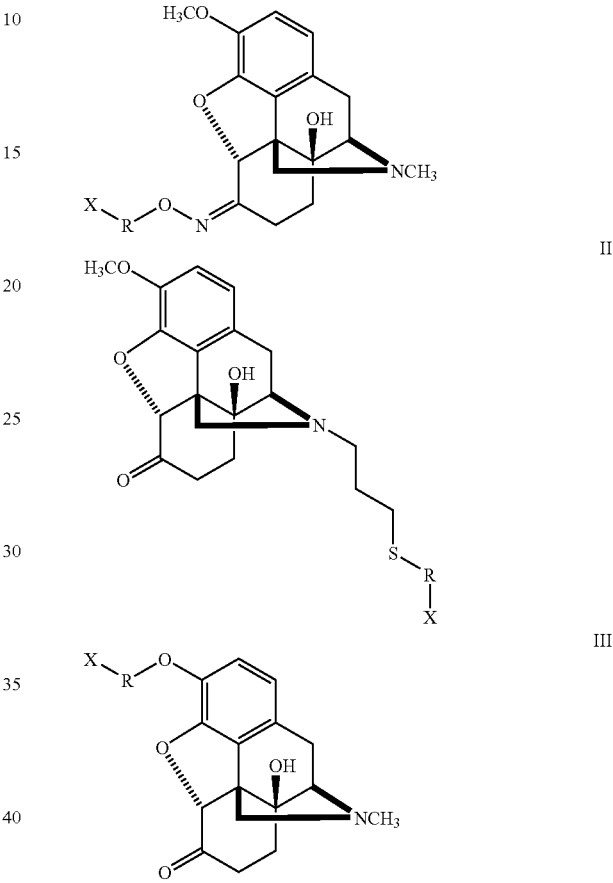

wherein R is a divalent alkyl, cycloalkyl or aryl group having 1 to 10 carbon atoms, and X is a functional group.

The functional group X can be used for coupling the haptens to carrier materials for the preparation of corresponding immunogens. The resulting immunogens are administered to mammalian hosts to elicit production of avid specific antisera, which are then used to develop sensitive immunoassays for the detection of oxycodone and its metabolites without showing cross-reactivity to other opiates such as morphine, codeine and heroin.

According to a second aspect of the invention, therefore, immunogens comprise haptens according to the present invention coupled to an antigenicity-conferring carrier material.

According to a third aspect of the present invention, novel antibodies are raised against the immunogens of the present invention, the antibodies being capable of binding with at least one structural epitope of oxycodone and its metabolites.

In a further aspect, conjugates of the present invention comprise haptens of the present invention covalently bound to a detectable labelling agent.

In a still further aspect of the present invention, a method is for detecting or determining oxycodone and its metabolites noroxycodone and oxymorphone without cross-reactivity to the other opiates in a sample. The method comprises contacting the sample with a conjugate of the present invention and with an antibody of the present invention, or a mixture thereof; detecting or determining bound conjugate and deducing from a calibration curve the presence of, or the amount of, oxycodone and its metabolites.

In a yet further aspect, in a kit for detecting or determining oxycodone and its metabolites, the kit includes a conjugate of the present invention and an antibody of the present invention. The kit may optionally include instructions for the use of the conjugate and the antibody for detecting or determining oxycodone and its metabolites in a sample. Preferably, the sample is a solution such as a biological fluid. More preferably, the sample is serum or urine.

DESCRIPTION OF PREFERRED EMBODIMENTS

The present invention relates to the preparation of the first hapten derivatives of oxycodone. These haptens are employed in the preparation of immunogens by coupling them to modified or non-modified immunogenic carrier materials. The immunogens obtained are then administered to mammalian hosts to elicit production of specific antibodies, which are then used to develop competitive immunoassays for oxycodone and its metabolites, employing hapten-labelling agents as conjugates (detection reagents).

In compounds of formulae I, II and III, R is preferably $C_{1-3}$ alkylene, e.g. $C_1$ in formula I, $C_2$ in formula II and $C_3$ in formula III. By way of example, X may be a carboxylic acid, maleimido, dithiopyridyl, thioacetyl, amino or aldehyde group, and is preferably carboxylic acid. Other suitable functional groups are known to those of ordinary skill in the art.

Preparation of Haptens

Haptens of the invention may be prepared by procedures known to those of ordinary skill in the art. The following embodiments can be modified as necessary, to prepare other compounds of the invention.

The hapten 6-carboxymethyloxime oxycodone (hapten A) may be prepared by reaction of oxycodone with carboxymethoxyamine hemihydrochloride in methanol at reflux in the presence of pyridine, according to the following scheme

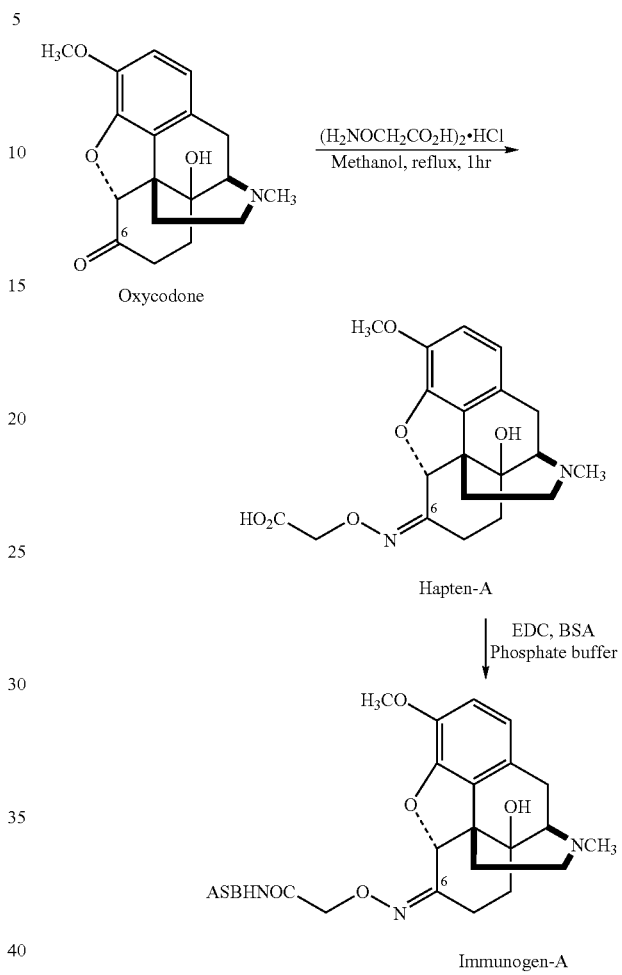

Hapten B may be prepared in three steps, according to the following scheme

-continued

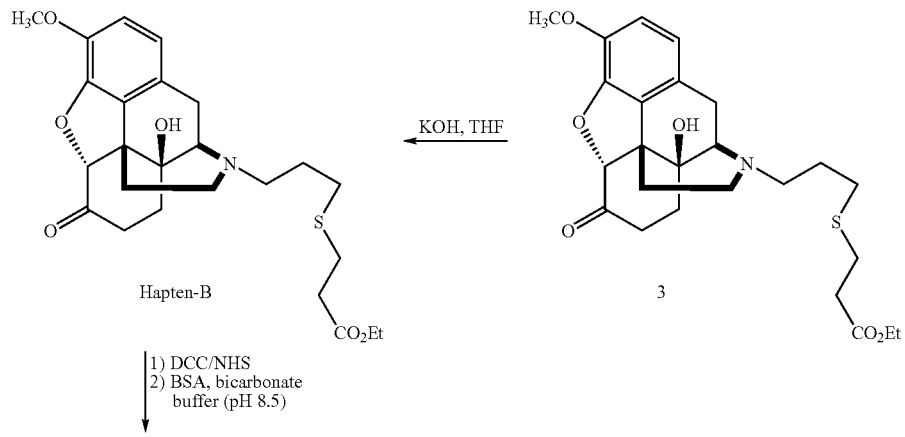

Hapten-B

1) DCC/NHS
2) BSA, bicarbonate buffer (pH 8.5)

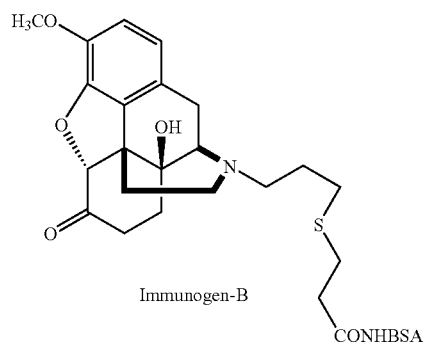

Immunogen-B

The above synthesis starts from the non-controlled substance naloxone 1. The reaction of naloxone 1 (free base) with methyl iodide, in dimethylformamide (DMF), in the presence of potassium carbonate, gives N-allyl noroxycodone 2. The ester-functionalised noroxycodone 3 is prepared by the reaction of ethyl 3-merraptopropionate (thiol-functionalised carboxylic ester) with the double bond located on N-allyl noroxycodone 2, in the presence of 2,2'-azobisisobutyronitnle (AIBN) as the initiating free radical source, in a chlorinated solvent by heating at reflux. The N-[S-(carboethoxyethyl)thioethyl]noroxycodone 3 is saponified in alkaline conditions by using potassium hydroxide in a mixture of tetrahydrofuran/water to give hapten B in good yield.

The 3-O-(3'-carboxypropyl)oxymorphone (hapten C) may be prepared in two steps from oxymorphone, according to the following scheme

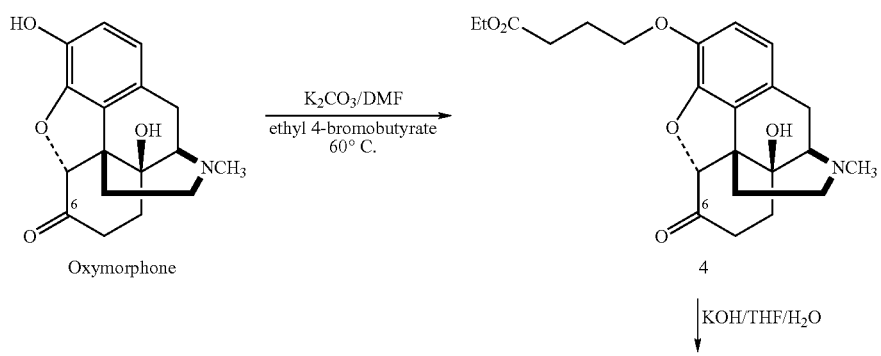

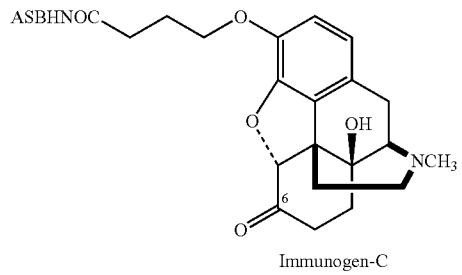

Immunogen-C

1) DCC/NHS, DMF
2) BSA, bicarbonate buffer (pH 8.5)

-continued

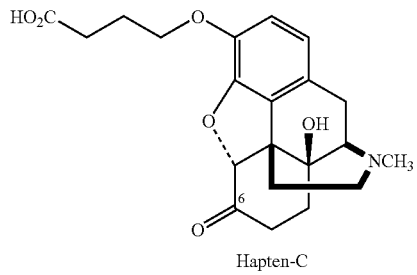

Hapten-C

The reaction of oxymorphone with ethyl-4-bromobutyrate in DMF, in the presence of potassium carbonate at 60° C., gives 3-O-[ethyl-3'-(carboxypropyl)]oxymorphone 4. Hapten C is obtained after saponification of the ester 4 with potassium hydroxide in tetrahydrofuran.

Preparation of Immunogens and Conjugates

Although the haptens of the present invention provide defined structural epitopes, they are not in themselves immunogenic and therefore need to be conjugated to carrier materials that will elicit an immunogenic response when administered to a host animal. Each hapten of the present invention can also be coupled to a labeling agent such as an enzyme, a substance having fluorescent properties or a radioactive label for the preparation of detection reagents for use in immunoassays. The conjugation of haptens A, B and C may be performed without prior modification of the carrier material or labeling agent using standard methods of conjugation such as mixed anhydride, EDC or succinimidyl activation of the haptens. These and other procedures are generally known to those of ordinary skill in the art.

For immunogens of the invention, suitable carrier materials include proteins such as albumins, serum proteins e.g. globulins, ocular lens proteins and lipoproteins. Illustrative protein carriers include bovine serum albumin (BSA), egg ovalbumin, bovine gamma globulin, thyroxine binding globulin and keyhole limpet haemocyanin (KLH). Alternatively, synthetic poly(amino acids) having a sufficient number of available amine groups such as lysine may be employed, as may other synthetic or natural polymeric materials bearing reactive functional groups. In particular, carbohydrates, yeasts or polysaccharides may be conjugated to the hapten to produce an immunogen. Preferably, the carrier material is a protein, a protein fragment, a synthetic polypeptide or a semi-synthetic peptide.

Preferably, the labelling agent in a conjugate of the invention is an enzyme, a luminescent substance, a radioactive substance or a mixture thereof. More preferably the enzyme is a peroxidase, most preferably horseradish peroxidase (HRP). Alternatively, or additionally, the luminescent substance may be bioluminescent, chemiluminescent or fluorescent.

In preparing immunogens or conjugates with haptens of the present invention where a thiol functional group is present, maleimido, halo, pyridyldithio or vinylsulphone groups may first be introduced to the carrier material or labeling agent (enzyme or label) using heterobifunctional linkers such as: N-(g-maleimidobutyryloxy)succinimide ester (GLBS); succinimidyl 4-(N-maleimidomethyl)cyclohexane-1-carboxylate (SMCC); (m-maleimidobenzoyl)-N-hydroxysuccinimide (MBS); succinimidyl 4-(p-maleimidophenyl)butyrate (SMPB); N-succinimidyl (4-iodoacetyl) aminobenzoate (SIAB); bromoacetylglycine N-hydroxysuccinimide; N-succinimidyl 3-(2-pyridyldithio) propionate (SPDP); or vinylsulphone (Pierce Chemical Company, USA). The thus-modified carrier material or labeling agent can then be conjugated via the thiol groups on the hapten.

In order to confirm that adequate conjugation of the hapten to carrier material has been achieved prior to immunization, each immunogen may be evaluated using matrix-assisted UV laser desorption/ionisation time-of-flight mass spectrometry (MALDI-TOF MS). Each of the immunogens of the present invention can be used for immunisation, in order to produce antibodies for the present invention.

General Procedure for MALDI-TOF Analysis of Immunogens

MALDI-TOF mass spectrometry may be performed using a Voyager STR Biospectrometry Research Station laser-desorption mass spectrometer coupled with delayed extraction. An aliquot of each sample to be analysed is diluted in 0.1% aqueous trifluoroacetic acid (TFA) to create 1 mg/ml sample solutions. Aliquots (1 ml) are analysed using a matrix of sinapinic acid and bovine serum albumin (Fluka) was used as an external calibrant.

Preparation of Antisera

Antibodies of the invention may be prepared by immunising an animal, preferably a vertebrate, most preferably a mammalian animal, by repeated administration of an immunogen according to the present invention, and collecting the resultant serum from the immunised animals. Preferably, the process further comprises fixing the serum antibodies to a backing substrate, preferably a solid support, most preferably a polystyrene solid support. Preferably, the antibodies are polyclonal. Alternatively, the antibodies are monoclonal.

In order to generate polyclonal antisera, each immunogen of the present invention is mixed with Freund's Adjuvant and the mixture is injected into the host animal, such as rabbit, sheep, mouse, guinea pig or horse. Further injections (boosts) are made and serum is sampled for evaluation of the antibody titer. When the optimal titer has been obtained; the host animal is bled to yield a suitable volume of specific antiserum. The degree of the antibody purification required depends on the desired application. For many purposes there is no requirement for purification, however, in other cases, such as when the antibody is to be immobilised on a solid support, purification steps can be taken to remove undesired material and eliminate non-specific binding.

The specific antibodies prepared in this invention are useful as reagents for immunoassays for the detection or determination of oxycodone and its metabolites noroxycodone and oxymorphone.

The following Examples illustrate the invention

EXAMPLE 1

6-Carboxymethyloxime Oxycodone (Hapten A)

To a solution of oxycodone hydrochloride (637.1 mg, 1.81 mmol) in 20 ml of anhydrous methanol under nitrogen, was added carboxymethoxyamine hemihydrochloride (594 mg, 2.7 mmol) and the mixture was heated at reflux. After 15 minutes a white solid started to form and heating was continued for 1 hour. The solution was then cooled to room temperature and the solid was filtered, washed with cold methanol and dried overnight to give 6-carboxymethyloxime oxycodone (hapten A) as a white solid (400 mg, 60%).

| M.P: | 245° C. (decomp.) |
|---|---|
| I.R. (KBr): | $v(cm^{-1})$ 3183.17, 3064.68, 1723.76, 1508, 1455.8 and 1616.9. |

EXAMPLE 2

N-Allyl Noroxycodone 1

The naloxone free base was prepared from (3.0 g, 7.5 mmol) of naloxone hydrochloride dihydrate. To a solution of the naloxone free base (2.5 g, 7.63 mmol) in dimethylformamide (50 ml) was added at 0° C. potassium carbonate (2.43 g, 0.0176 mol) and iodomethane (136 g, 0.0096 mol) and the mixture was stirred for two hours (tlc indicated reaction was complete). The solvent was removed under reduced pressure and the residue obtained was purified by flash chromatography on silica gel (10%methanol/chloroform) to give the N-allyl noroxycodone 1 (2.5 g, 96%) as a yellow oil.

| I.R. (film): | $v(cm^{-1})$ 3347.1, 3057.68, 1676.1 and 734.2 |
|---|---|
| $^{13}$C NMR (CDCl$_3$): | δ(ppm) 206, 140, 133, 127, 122, 117, 116, 112, 88, 69, 60, 55, 54, 48, 41, 34, 29, 28, 20. |

EXAMPLE 3

N-[S-(Carboethoxyethyl)thioethyl)]noroxycodone 2

To a solution of N-allyl noroxycodone 1 (2.099 g, 6.15 mmol) in 100 ml of anhydrous chloroform under nitrogen was added ethyl-mercaptopropionate (8.26 g, 61.5 mmol) and AIBN (207 mg, 1.23 mmol) and the resultant mixture was stirred at reflux for 20 hours. After cooling the mixture to room temperature, cyclohexene (2 ml) was added to stop the reaction and the stirring continued for one hour. The mixture was evaporated to dryness and the residue obtained was purified via flash chromatography on silica gel (10%methanol/chloroform) to give the title compound 2 as a clear oil (1.40 g, 49.2%).

| I.R (film): | $v(cm^{-1})$ 3387.5, 1728.5, 1256+ and 1048 |
|---|---|
| $^{13}$C NMR (CDCl$_3$): | δ(ppm) 208.4, 171.8, 145.0, 143.0, 129.5, 124.9, 119.4, 115.1, 90.3, 70.4, 63.4, 60.7, 56.9, 53.4, 50.7, 43.3, 36.1, 34.9, 31.5, 30.6, 30.2, 27.4, 23.2, 14.2. |

EXAMPLE 4

N-[S-(Carboxyethyl)thioethyl]noroxycodone (Hapten B)

N-[S-(Carboxyethoxyethyl)thioethyl]noroxycodone 2 (1.25 g, 2.7 ml) was dissolved in tetrahydrofuran (10 ml) and water (10 ml). Potassium hydroxide (471 mg, 8.4 mmol) was added and the mixture stirred for 3 hours at room temperature. The THF was removed under reduced pressure and the aqueous layer was neutralised with the aid of 1N hydrochloric acid. The solution was then evaporated to dryness and the residue obtained was added to 100 ml of 20% methanol in chloroform and the mixture stirred for 30 minutes. The mixture was then filtered to remove insoluble salts. The solvents were removed under reduced pressure and the crude mixture obtained was purified via flash chromatography on silica gel (10% methanol in chloroform) Rf 0.31 to give the desired product hapten B (810 mg, 69%) as a white foam.

| I.R. (KBr): | $v(cm^{-1})$ 3350, 3054.3, 2933.5, 2837.7, 1726.7, 1506.1, 1439.6, 1265.6, 737.0 and 702.5 |
|---|---|
| MS (EI+): | 447.2 |

EXAMPLE 5

3-O-(Carboethoxypropyl)oxymorphone 3

A suspension of oxymorphone (1 g, 3.3 mmol), ethyl-4-bromobutyrate (772 mg, 3.96 mmol), potassium carbonate (910.8 mg, 6.6 mmol) and a few crystals of potassium Iodide in anhydrous DMF (30 ml) was heated at 60° C. with stirring under nitrogen overnight. After cooling to room temperature, the precipitate was removed by filtration and the solution concentrated under reduced pressure. The residue obtained was purified via flash chromatography on silica gel (10% methanol in chloroform) to give the desired compound (845 mg, 61.6%) as an oil.

EXAMPLE 6

3-O-(3'-Carboxypropyl)oxymorphone (Hapten C)

Compound 3 (800 mg, 1.93 mmol) was dissolved in a 1/1 mixture of THF/water (20 ml). Potassium hydroxide (323 mg, 5.8 mmol) was added and the mixture stirred at room temperature for 2 hours. The THF was removed under reduced pressure and the pH of the aqueous phase was adjusted to pH 7 with the aid of 1N hydrochloric acid. The mixture was then concentrated to dryness and the residue obtained was purified via flash chromatography on silica gel (25% methanol in chloroform) to give hapten C (532 mg, 71%) as a white solid.

EXAMPLE 7

Conjugation of Hapten A to BSA (Immunogen-A)

105 mg EDC.hydrochloride was dissolved in water (0.5 ml) and immediately added to a solution of hapten A (85.4 mg, 0.22 mmol) in DMF (1 ml). After mixing, this solution was added to a solution of BSA (200 mg) in water (10 ml). Sulfo-NHS (52 mg) was immediately added and the reaction mixture was incubated, with stirring at room temperature, overnight. The mixture was then dialysed against 50 mM phosphate buffer pH 7.2 (3 changes) for 24 hrs, and freeze-dried.

MALDI results showed 10.0 molecules of hapten A had been conjugated to one molecule of BSA.

EXAMPLE 8

Conjugation of Hapten B to BSA (Immunogen-B)

To a solution of N-[S-(carboxyethyl)thioethyl]noroxycodone (hapten B) (57.8 mg, 0.11 mmol) in DMF (1 ml) was added N,N-dicyclohexylcarbodimide (DCC) (38 mg, 0.19 mmol) and N-hydroxysuccinimide (21.2 mg, 0.19 mmol) and the mixture was stirred at room temperature overnight. The dicyclohexylurea formed was removed by filtration and the solution was added dropwise to a solution of BSA (150 mg) in 50 mM sodium bicarbonate solution (pH 8.5) (6 ml). The mixture was stirred overnight at 4° C. The solution was then dialysed against 50 mM phosphate buffer pH7.2 (3 changes) for 24 hours at 4° C. and freeze-dried.

MALDI results showed 40.2 molecules of hapten B had been conjugated to one molecule of BSA.

EXAMPLE 9

Conjugation of Hapten C to BSA (Immunogen-C)

Immunogen C was prepared by the same method as Immunogen B (Example 8) by using the 3-O-carboxypropyl)oxymorphone and BSA.

EXAMPLE 10

General Method for Conjugation of Haptens A, B and C to HRP 10 mg of EDC.hydrochloride was dissolved in water (0.5 ml) and immediately added to a solution of hapten (2 mg) in DMF (0.2 ml). After mixing, this solution was added dropwise to a solution of HRP (20 mg) in water (1 ml). Sulfo-NHS (5 mg) was added and the reaction mixture was incubated in the dark at room temperature overnight. Excess hapten was removed by desalting with 2 PD-10 columns (Pharmacia) in series, pre-equilibrated with PBS at pH 7.2. The hapten-HRP conjugate was then dialysed overnight against 10 L of PBS pH7.2 at 4° C.

EXAMPLE 11

Antibodies to Immunogens A and B

Aqueous solutions of the immunogens prepared in Examples 7 and 8 were formulated with Freund's Complete Adjuvant (FCA) to form emulsions consisting of 4 mg/ml immunogen A and 2 mg/ml immunogen B in 50% (v/v) FCA. Three sheep were immunized with each emulsion (1° immunizations), 0.25 ml being subcutaneously injected at each of four sites in the flank of each animal. The next immunizations (first boosts) contained 2 mg/ml immunogen A and 1 mg/ml immunogen B. Subsequent immunizations (boosts 2 to 25) contained 1 mg/ml of each immunogen. All boosts were emulsified in 50% (v/v) Freund's Incomplete Adjuvant (FIA) and administered to the appropriate sheep in the same manner as the 1° immunizations, at monthly intervals for 1 year. Blood sampling took place 7 to 14 days after each boost. Each sample was processed to produce antiserum which was further purified by caprylic acid and ammonium sulfate precipitation to yield an immunoglobulin G (IgG) fraction. The IgG fraction was evaluated by competitive ELISA microtiter plate assay, as described in Example 12 below.

EXAMPLE 12

Competitive ELISAs for Oxycodone and its Metabolites (a) The wells of an enhanced binding 96-well polystyrene microtiter plate were coated with the IgG fraction of the antiserum raised to immunogen A (hapten A-BSA) (Example 7), diluted in 10 mM Tris, pH8.5 (125 µl/well). The appropriate antibody coating dilution was determined using standard ELISA chequerboard techniques. The plate was incubated for 2 hours at 37° C., washed 4 times with Tris-buffered saline containing Tween 20 (TBST) and tapped dry. Standard solutions of oxycodone and its metabolites were prepared in TBST at 0, 0.5, 1, 5, 25, 100, 250 and 500 ng/ml and 50 µl of each was added to each of three wells. 75 µl of conjugate A (hapten A-HRP) (Example 10), diluted in Tris buffer containing EDTA, D-mannitol, sucrose, thimerosal and BSA, was added to each of the wells. The appropriate dilution of conjugate was also determined using standard ELISA chequerboard techniques. The plate was incubated at 37° C. for 2 hours. The excess unbound conjugate was removed by washing 6 times over a 10 minute period with TBST. 125 µl of tetramethylbenzedine (TMB) substrate solution was added to each well of the plate that was then incubated for 15 to 20 minutes in the dark at room temperature. The reaction was terminated by addition of 125 µl 0.2M $H_2SO_4$ to each well. The absorbance was then measured at 450 nm using a microtiter plate reader. The data generated in the assay are presented in Table 1.

TABLE 1

| Standard Concentration | Oxycodone | | Noroxycodone | | Oxymorphone | |
|---|---|---|---|---|---|---|
| ng/ml | $A_{450}$ | % $B/B_0$ | $A_{450}$ | % $B/B_0$ | $A_{450}$ | % $B/B_0$ |
| 0 | 2.467 | 100.0 | 2.307 | 100.0 | 2.325 | 100.0 |
| 0.5 | 2.185 | 88.6 | 2.290 | 99.3 | 2.162 | 93.0 |
| 1 | 2.028 | 82.2 | 2.312 | 100.2 | 2.103 | 90.5 |
| 5 | 1.464 | 59.3 | 2.314 | 100.3 | 1.747 | 75.1 |
| 25 | 0.891 | 36.1 | 2.292 | 99.3 | 1.328 | 57.1 |
| 100 | 0.547 | 22.2 | 2.254 | 97.7 | 0.912 | 39.2 |
| 250 | 0.366 | 14.8 | 2.217 | 96.1 | 0.679 | 29.2 |
| 500 | 0.249 | 10.1 | 2.141 | 92.8 | 0.567 | 24.4 |
| $IC_{50}$ | 8.7 ng/ml | | >500.0 ng/ml | | 32.8 ng/ml | |
| % CR | 100.0 | | <1.7 | | 26.5 | |

$A_{450}$ = absorbance at 450 nm
B = absorbance at 450 nm at xng/ml standard concentration
$B_0$ = absorbance at 450 nm at 0ng/ml standard concentration
$IC_{50}$ = standard concentration which produces 50% $B/B_0$
% CR = percentage cross-reactivity based on specificity to oxycodone (b) In a similar manner to that described in Example 12(a), the wells of a 96-well microtiter plate were coated with the IgG fraction of the antiserum raised to immunogen B (hapten B-BSA) (Example 8), standards were applied at 0, 10, 50, 100, 250, 300, 1000 and 200 ng/ml and conjugate B (hapten B-HRP) (Example 10) was employed as detection reagent. The data generated are presented in Table 2. The same definitions apply for $A_{450}$, B, $B_0$ and $IC_{50}$.

TABLE 2

| Standard Concentration | Oxycodone | | Noroxycodone | | Oxymorphone | |
|---|---|---|---|---|---|---|
| ng/ml | $A_{450}$ | % $B/B_0$ | $A_{450}$ | % $B/B_0$ | $A_{450}$ | % $B/B_0$ |
| 0 | 2.217 | 100.0 | 2.412 | 100.0 | 2.332 | 100.0 |
| 10 | 1.679 | 75.7 | 2.187 | 90.7 | 2.421 | 103.8 |
| 50 | 1.111 | 50.1 | 1.709 | 70.9 | 2.270 | 97.3 |
| 100 | 0.928 | 41.9 | 1.569 | 65.0 | 2.216 | 95.0 |
| 250 | 0.578 | 26.1 | 1.254 | 52.0 | 2.181 | 93.5 |
| 500 | 0.394 | 17.8 | 1.053 | 43.7 | 2.101 | 90.1 |
| 1000 | 0.271 | 12.2 | 0.785 | 32.5 | 1.964 | 84.2 |
| 2000 | 0.185 | 8.3 | 0.588 | 24.4 | 1.788 | 76.7 |
| $IC_{50}$ (ng/ml) | 54.7 | | 233.5 | | >2000.0 | |
| % CR | 100.0 | | 23.4 | | <2.7 | |

EXAMPLE 14

Cross-reactivity of Competitive ELISAs for Oxycodone and its Metabolites with Other Opiates In order to determine the specificity of the competitive ELISAs for oxycodone and its metabolites, standard solutions of the opiates morphine, codeine, morphine-3-glucuronide, 6-monoacetylmorphine, hydromorphone, hydrocodone, dihydrocodone and thebaine were prepared in TBST at 0, 0.5, 1, 5, 25, 100, 250 and 500 ng/ml for the immunoassay described in Example 12(a) and at 0, 10, 50, 100, 250, 500, 1000 and 2000 ng/ml for the immunoassay described in Example 12(b). Employing each series of standards in the oxycodone competitive ELISAs, calibration curves were generated and these were used to determine the cross-reactivity of the immunoassays with these opiates. The results of this study are presented in Table 3, cross-reactivity being calculated according to the following formula:

%CR=$IC_{50, \, Oxycodone}/IC_{50, \, OP} \times 100$ where %CR is the percentage cross-reactivity, $IC_{50, \, Oxycodone}$ is the concentration of Oxycodone that causes 50% displacement of signal and $IC_{50, \, Op}$ is the concentration of test opiate that causes 50% displacement of signal.

TABLE 3

| | Example 13 (a) | | Example 13 (b) | |
|---|---|---|---|---|
| Opiate | $IC_{50, \, OP}$ (ng/ml) | % CR | $IC_{50, \, OP}$ (ng/ml) | % CR |
| Morphine | >500 | <1.7 | >2000 | <2.7 |
| Codeine | 386.7 | 2.2 | >2000 | <2.7 |
| Morphine-3-glucuronide | >500 | <1.7 | >2000 | <2.7 |
| 6-Monoacetylmorphine | >500 | <1.7 | >2000 | <2.7 |
| Hydromorphone | >500 | <1.7 | >2000 | <2.7 |
| Hydrocodone | >500 | <1.7 | 72.4 | 75.6 |
| Dihydrocodone | >500 | <1.7 | >2000 | <2.7 |
| Thebaine | 203.2 | 4.3 | >2000 | <2.7 |

What is claimed is:

1. A compound of formula

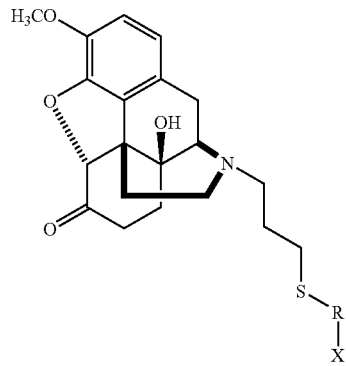

wherein R is a divalent alkyl, cycloalkyl or aryl group having 1 to 10 carbon atoms, and X is a functional group.

2. A compound according to claim 1, wherein R is $C_{1-3}$ alkylene.

3. A compound according to claim 1, wherein X is COOH.

4. A compound according to claim 1, which is N-[S-(carboxyethyl)thiopropyl]noroxycodone.

5. An immunogen comprising a compound according to claim 1, coupled to an antigenic carrier.

6. An antibody raised against an immunogen according to claim 5, and capable of binding with at least one epitope of oxycodone and its metabolites.

7. A conjugate comprising a compound according to claim 1 covalently bound to a detectable label.

8. A method for detecting or determining oxycodone and its metabolites in a sample, which comprises contacting the sample with a conjugate comprising a compound according to claim 1 covalently bound to a detectable label and an antibody raised against an immunogen comprising the compound of claim 1 coupled to an antigenic carrier, and being capable of binding with at least one epitope of oxycodone and its metabolites, and detecting bound conjugate.

9. A kit for determining the presence or amount of oxycodone and its metabolites in a sample, which includes a conjugate comprising a compound according to claim 1 covalently bound to a detectable label and an antibody raised against an immunogen comprising the compound of claim 1 coupled to an antigenic carrier, and being capable of binding with at least one epitope of oxycodone and its metabolites.

10. A compound according to claim 2, wherein X is COOH.

11. An immunogen comprising a compound according to claim 2, coupled to an antigenic carrier.

12. An immunogen comprising a compound according to claim 3, coupled to an antigenic carrier.

13. An immunogen comprising a compound according to claim 4, coupled to an antigenic carrier.

14. A conjugate comprising a compound according to claim 2 covalently bound to a detectable label.

15. A conjugate comprising a compound according to claim 3 covalently bound to a detectable label.

16. A conjugate comprising a compound according to claim 4 covalently bound to a detectable label.

* * * * *